United States Patent [19]

Singh et al.

[11] Patent Number: 5,260,449
[45] Date of Patent: Nov. 9, 1993

[54] METHOD FOR PREPARING 7-OXABICYCLOHEPTYL SUBSTITUTED BROMOOXAZOLE AMIDE PROSTAGLANDIN ANALOG INTERMEDIATES USEFUL IN THE PREPARATION OF ANTI-THROMBOTIC AND ANTI-VASOSPASTIC COMPOUNDS

[75] Inventors: Janak Singh, Lawrenceville; Richard H. Mueller, Ringoes; Jagabandhu Das, Hamilton Square; Philip M. Sher, Plainsboro, all of N.J.

[73] Assignee: E. R. Squibb & Sons, Inc., Princeton, N.J.

[21] Appl. No.: 928,394

[22] Filed: Aug. 12, 1992

[51] Int. Cl.$^5$ .......................... C07D 413/04
[52] U.S. Cl. .................... 548/236; 549/263
[58] Field of Search .......... 548/236; 549/463; 570/252, 234

[56] References Cited

U.S. PATENT DOCUMENTS 2,490,424 12/1949 Ferguson .......................... 570/234
5,100,889 3/1992 Misra et al. ...................... 548/236
5,158,967 10/1992 Hall ................................. 549/463

FOREIGN PATENT DOCUMENTS 476994 3/1992 European Pat. Off. .

OTHER PUBLICATIONS

Misra et al, "Thromboxane Receptor Antagonist BMS-180291: A New Pre-Clinical Lead," Bioorganic and Medicinal Chemistry, vol. 2, No. 1, pp. 73-76, 1992.

Primary Examiner—Donald G. Daus
Attorney, Agent, or Firm—Burton Rodney

[57] ABSTRACT

A method is provided for preparing bromooxazole intermediates of the structure

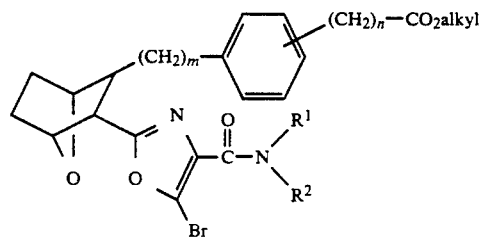

wherein a vinyl compound of the structure

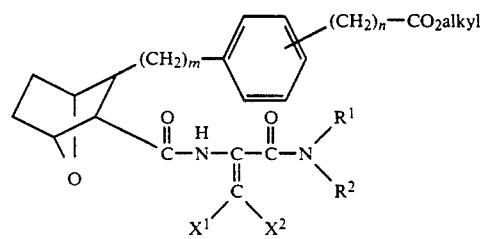

wherein $X^1$ and $X^2$ are independently H and Br, is treated with a metal halide such as cupric bromide, and a base such as 1,8-diazabicyclo-[5.4.0]undec-7-ene (DBU). The resulting bromooxazole may be hydrolyzed and hydrogenolyzed to the final anti-thrombotic-anti-vasospastic compounds.

29 Claims, No Drawings

METHOD FOR PREPARING 7-OXABICYCLOHEPTYL SUBSTITUTED BROMOOXAZOLE AMIDE PROSTAGLANDIN ANALOG INTERMEDIATES USEFUL IN THE PREPARATION OF ANTI-THROMBOTIC AND ANTI-VASOSPASTIC COMPOUNDS

FIELD OF THE INVENTION

The present invention relates to a method for preparing a novel 7-oxabicycloheptyl substituted bromooxazole amide prostaglandin analog intermediate by cyclization of a corresponding vinyldiamide or vinylbromide compound employing a metal halide such as cupric bromide, in combination with a base such as DBU. The resulting oxazole may be hydrolyzed and hydrogenolized to a final anti-thrombotic-anti-vasospastic product.

BACKGROUND OF THE INVENTION

U.S. Pat. No. 5,100,889 to Misra et al discloses 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic diseases, and have good duration of action. Examples of compounds disclosed in Misra et al have the structural formula I

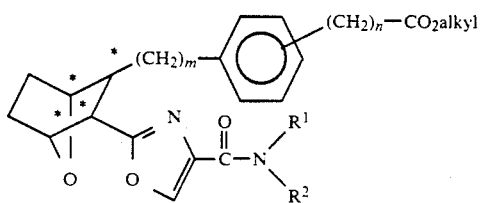

and including all stereoisomers thereof, wherein
m is 1, 2 or 3; n is 0, 1, 2, 3 or 4;
$R^1$ is hydrogen, lower alkyl, aralkyl, aryl, cycloalkyl, cyclo-alkylalkyl, or amide

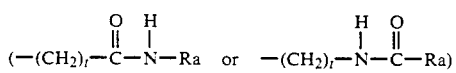

wherein t is 1 to 12 and $R_a$ is lower alkyl, aryl, cycloalkyl, or cycloalkylalkyl);
$R_2$ is hydrogen, lower alkyl, aryl, or aralkyl; or $R^1$ and $R^2$ together with the nitrogen to which they are linked may form a 5- to 8- membered ring.

Misra et al disclose that these compounds may be prepared from the oxazoline XV'

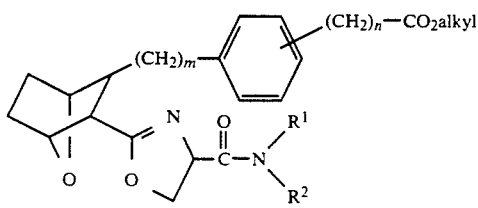

which is made to undergo oxidation using manganese dioxide, or nickel peroxide, or preferably cupric bromide and 1,8-diazabicyclo[5.4.0]undec-7-ene (DBU) to form the oxazole I.

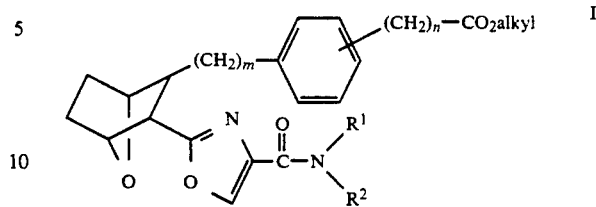

The cupric bromide oxidation is carried out at a temperature of within the range of from about 20° C. to about 70° C., employing a molar ratio of cupric bromide to XV' of within the range of from about 2:1 to about 6:1 and a molar ratio of cupric bromide to DBU of within the range of from about 1:1 to about 1:3 in an inert solvent, preferably ethyl acetate/chloroform (1:1, v/v).

The so-formed oxazole may then be hydrolyzed by treatment with an aqueous solution of alkali metal base and then aqueous acid to form the corresponding acid.

In Example 1 Part O of Misra et al. the methyl ester of the final product is prepared together with the corresponding bromooxazole as a side product (6% yield).

DESCRIPTION OF THE INVENTION

In accordance with the present invention, a method is provided for preparing oxazoles of formula I (as set out above in the Misra et al patent) which includes the step of treating a vinyl compound, such as a vinyl diamide, vinyl bromide, or vinyl dibromide of the structure II

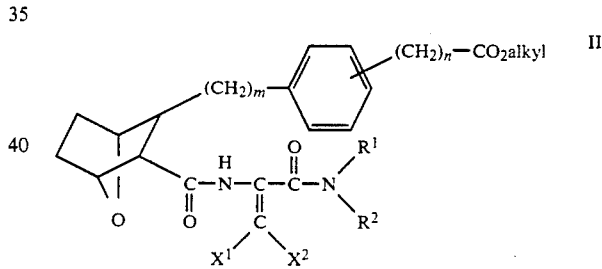

wherein $X^1$ and $X^2$ are independently selected from H and Br and wherein m, n, $R^1$ and $R^2$ are as defined below (and as in the above-mentioned Misra et al patent), with a metal halide such as cupric bromide, cuprous bromide or ferric bromide, preferably cupric bromide, and a base which is 1,8-diazabicyclo[5.4.0]undec-7-ene (DBU) or 1,5-diazabicyclo[4.3.0]non-5-ene (DBN), preferably DBU, in the presence of an inert organic solvent such as dichloromethane, chloroform, ethyl acetate/chloroform, or dimethylformamide (DMF), to form the corresponding bromooxazole III

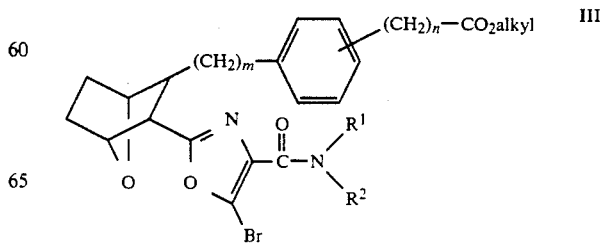

The so-formed bromooxazole III may be subjected to hydrogenolysis, for example, by treatment of III with hydrogen in the presence of a catalyst such as Pd-C, and an alcohol solvent such as ethanol or methanol, to form the corresponding oxazole ester I.

In the above formulae I, II and II compounds,
n is 0, 1, 2, 3 or 4;
m is 1, 2 or 3;
$R^1$ is hydrogen, lower alkyl, aryl, aralkyl, cycloalkyl, cycloalkylalkyl or an amide

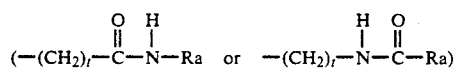

wherein t is 1 to 12 and Ra is lower alkyl, aryl, cycloalkyl or cycloalkylalkyl);

$R^2$ is hydrogen, lower alkyl, aryl, or aralkyl; or $R^1$ and $R^2$ together with the N to which they are linked form a 5- to 8-membered ring which contains only the single N heteroatom.

Oxazole ester I may be hydrolyzed to the corresponding acid by treatment of I with alkali metal base and then with aqueous acid as described in U.S. Pat. No. 5,100,889.

Alternatively, bromooxazole ester III may be hydrolyzed by treatment with an alkali metal hydroxide such as NaOH, KOH or LiOH and then strong acid such as HCl, $H_2SO_4$ or phosphoric acid, to form the corresponding bromooxazole acid IIIA.

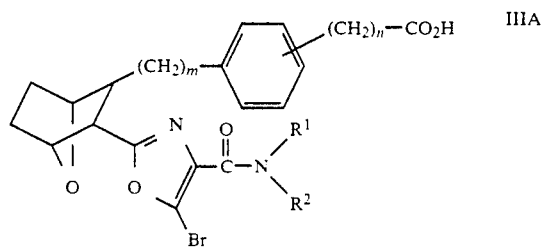

Bromooxazole acid IIIA may then be subjected to hydrogenolysis by treating IIIA with weak aqueous base such as sodium bicarbonate, potassium bicarbonate, sodium carbonate and the like and with hydrogen in the presence of a reduction catalyst such as Pd-C, to form the corresponding salt which may be treated with acid such as HCl to form the corresponding acid.

Alternatively, bromooxazole acid IIIA may be directly hydrogenolized to the acid product of the invention I by treating IIIA with hydrogen in the presence of a reduction catalyst such as Pd-C.

DETAILED DESCRIPTION OF THE INVENTION

In carrying out the method of the invention, the reaction of the vinyl compound II, namely, vinyl diamide, vinyl bromide or vinyl dibromide of the structure II, with the metal halide is carried out at a temperature within the range of from about 20° C. to 70° C., preferably from about 10 to about 25° C., preferably under an inert atmosphere such as argon or nitrogen.

The metal halide is employed in a molar ratio to vinyl compound II of within the range of from about 2.5:1 to about 5:1, preferably from about 3:1 to about 4:1, and most preferably about 4:1; and the base is employed in a molar ratio to vinyl compound II of within the range of from about 2.5:1 to about 5:1, preferably from about 3:1 to about 4:1, and most preferably about 4:1.

The above reaction will be carried out for a period of from about 5 to about 150 hours, preferably from about 18 to about 48 hours.

In the above method, the preferred metal halide is cupric bromide, the preferred base is DBU and the preferred solvent is dichloromethane.

The starting vinyl compound II wherein one of $X^1$ and $X^2$ is H and the other Br, that is vinyl bromide IIA.

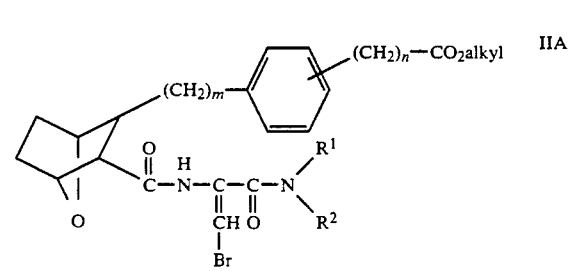

is prepared as follows.
The diamide IV

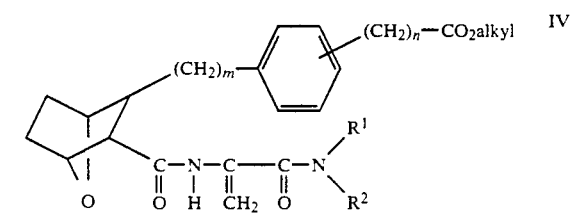

wherein m, n, $R^1$ and $R^2$ are as defined above is treated with a bromine source such as $Br_2$ or N-bromosuccinamide followed by treatment with an amine base, such as triethylamine, diisopropyl ethylamine or tributylamines, at a reduced temperature, under an inert atmosphere, such as argon, to form the vinyl bromide compound IIA (one of $X^1$ and $X^2$ is H and the other is Br)d, which is then employed as described above to form oxazole I.

The starting vinyl compounds II wherein each of $X^1$ and $X^2$ are Br, that is vinyl dibromide IIB

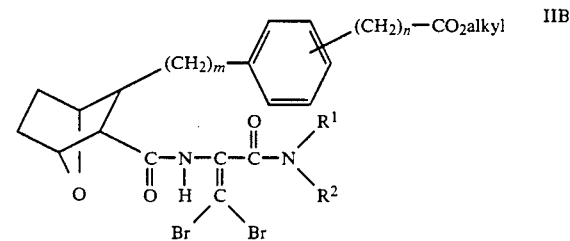

are novel compounds and are prepared as follows.

A solution of vinyl bromide compound IIA (wherein one of $X^1$ and $X^2$ is Br and the other H) in a dry inert organic solvent, such as dichloromethane, chloroform or dichloroethane is cooled to a temperature within the range of from about −40° to about −80° C. and treated with bromine and organic bases such as triethylamine, diisopropylethylamine or tributylamine to form the vinyl dibromide compound IIB.

In carrying out the above reaction, Br$_2$ is employed in a molar ratio to IIA of within the range of from about 1:1 to about 1.5:1, preferably from about 1:1 to about 1.2:1.

The starting diamide IV may be prepared as follows. Hydroxymethyl compound of the structure V

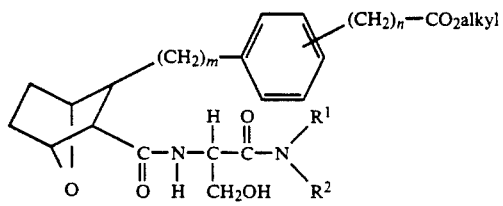

(prepared as described in Misra et al U.S. Pat. No. 5,100,889) is treated with methanesulfonyl chloride (mesyl chloride) in the presence of an organic base such as triethylamine, diisopropylethylamine or tributylamine, to form the mesylate VI

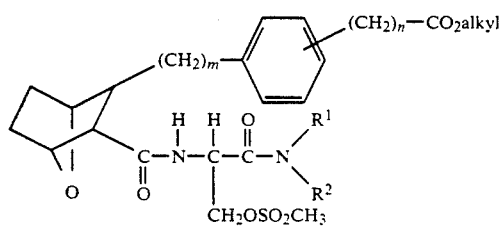

and mesylate VI is subjected to a displacement reaction wherein VI is treated with an alkali metal salt such as lithium chloride or a quaternary ammonium salt such as benzyltributyl ammonium chloride, to from the chloromethyl amide VII

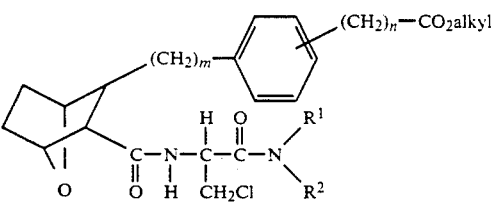

In an alternative method for preparing the chloromethyl amide VII, an amide of the structure VIII (formed from the corresponding amide)

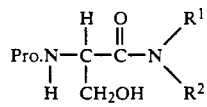

wherein Pro represents a protecting group, such as t-butyloxycarbonyl, benzyloxycarbonyl and the like, and R$^1$ and R$^2$ are as defined above, is treated with an organic base such as triethylamine, diisopropylethylamine or tributylamine, and methanesulfonyl chloride at a reduced temperature to form the mesylate IX

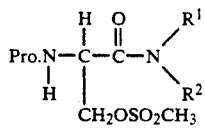

Mesylate IX is subjected to a displacement reaction wherein IX is treated with an alkali metal salt such as lithium chloride or a quaternary ammonium salt such as benzyltributyl ammonium chloride, at an elevated temperature of from about 40° to about 65° C. to form chloromethyl compound X

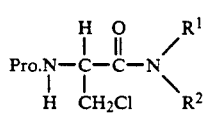

Chloromethyl compound X is treated with a deprotecting agent to form the chloromethyl amine XI

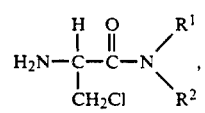

and XI is coupled with acid XII

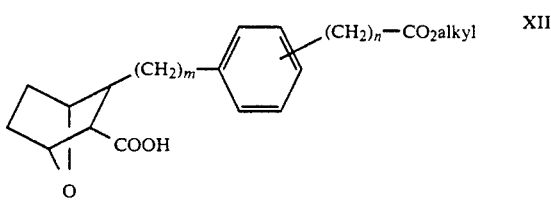

in the presence of 1-(3-dimethylaminopropyl)-3-ethylcarbodiimide hydrochloride (WSC) or dicyclohexylcarbodiimide (DCC), and 1-hydroxybenzotriazole (HOBT), in the presence of N-methylmorpholine (NMM), to form the chloromethylamide VII.

Alternatively, the acid XII can be converted to the corresponding acid chloride by treatment with oxalyl chloride, preferably in the presence of a catalytic amount of N,N-dimethylformamide, which acid chloride is treated with amine XI in the presence of an acid scavenger such as triethylamine or DBU, or sodium bicarbonate (when employing aqueous conditions) to form chloromethylamide VII.

The chloromethyl amide VII is treated with DBU under an inert atmosphere, such as argon, to form the vinyl diamide IV which is then employed as described above, in accordance with the present invention, to form oxazole I.

Preferred vinyl compound starting materials will comprise those of Formulae II, IIA, IIB or IV wherein m is 1 or 2 and n is 1, 2 or 3, R$^1$ is alkyl of from 3 to 7 carbons and R$^2$ is hydrogen or alkyl of from 3 to 7 carbons.

Where the starting vinyl bromide IIA (wherein one of X$^1$ and X$^2$ is Br and the other is H) is prepared starting with vinyl diamide IV, diamide IV which is treated with a bromine source such as Br$_2$ or N-bromosuccinamide, preferably Br$_2$, at a reduced temperature of within the range of from about −80° to about −40° C., and preferably from about −80° to about −60° C., under an inert atmosphere such as argon or nitrogen, preferably argon, employing a molar ratio of bromine source to diamide IV of within a range of from about 1:1 to about 2:1 and preferably from about 1:1 to about 1.1:1. The organic base, which may be triethylamine, DBU, Hunig's base (diisopropylethyl amine), collidine, dimethylamino pyridine or pyridine, preferably triethylamine, will be admixed with the reaction mixture at a temperature of within the range of from about −78° C. to about 25° C. and preferably from about −20° C. to about 0° C. The above reaction will be carried out in the presence of an inert organic solvent such as methylene chloride, chloroform, tetrahydrofuran (THF), acetonitrile, or acetone, preferably methylene chloride.

In a first method for preparing starting vinyl diamide IV (employing chloromethyl amide VII), hydroxymethyl compound V (prepared as described in U.S. Pat. No. 5,100,889) will be treated with mesyl chloride employing a molar ratio of mesyl chloride to amide VII of within the range of from about 1:1 to about 3:1, and preferably from about 1:1 to about 1.5:1, in the presence of an organic base such as triethylamine or pyridine, preferably triethylamine, in the presence of an inert organic solvent such as methylene chloride or THF, at a temperature of within a range of from about −78° C. to about 0° C. and preferably from about −20° C. to about 0° C. to form mesylate VI.

The mesylate VI will be subjected to a displacement reaction by treatment with an alkali metal salt such as lithium chloride, sodium chloride, potassium chloride, lithium bromide or sodium iodide, preferably lithium chloride, or with a quaternary ammonium salt such as benzyltributyl ammonium chloride, tetra-n-butylammonium bromide, or tetra-n-butylammonium iodide, employing a molar ratio of salt to VI within the range of from about 2:1 to about 10:1, preferably from about 2:1 to about 5:1, the above reaction being carried out in the presence of an inert organic solvent such as dimethylformamide, THF, acetone, chloroform or methylene chloride, preferably dimethylformamide or methylene chloride.

Where the starting diamide IV is prepared starting with the chloromethylamide VII, DBU will be employed in a molar ratio to amide VII of within the range of from about 1:1 to about 4:1, preferably from about 1:1 to about 2:1, and the reaction will be carried out under an inert atmosphere such as argon or nitrogen.

In the alternative method for preparing vinyl diamide IV, the starting amide VIII (prepared as described in U.S. Pat. No. 5,100,889) will include a protecting group which can be t-butyloxycarbonyl (BOC) or trichloroethoxy carbonyl, preferably BOC, and will be treated with an organic base such as triethylamine, or pyridine, preferably triethylamine, and methanesulfonyl chloride at a reduced temperature of within the range of from about −78° C. to about 0° C. and preferably from about −20° C. to about 0° C. to form the mesylate IX. The methanesulfonyl chloride will be employed in a molar ratio to amide VIII of within the range of from about 1:1 to about 5:1, preferably from about 1:1 to about 2:1.

The mesylated compound IX will then be subjected to a displacement reaction employing an alkali metal salt such as lithium chloride, sodium chloride, potassium chloride, preferably lithium chloride, which is reacted with IX at an elevated temperature of from about 40° C. to about 100° C., and preferably from about 40° C. to about 65° C., to form the chloromethyl compound X. The alkali metal salt will be employed in a molar ratio to X of within the range of from about 2:1 to about 10:1, preferably from about 2:1 to about 5:1.

The chloromethyl compound X will be deprotected by reaction with a deprotecting agent such as trifluoroacetic acid, anhydrous hydrogen chloride/dioxane, preferably trifluoroacetic acid, employing a molar ratio of deprotecting agent to X of within the range of from about 5:1 to about 20:1, preferably from about 5:1 to about 10:1 to form the chloromethyl amine compound XI.

Chloromethyl amine XI is coupled with acid XII employing a molar ratio of XI:XII of within the range of from about 1:1 to about 3:1, preferably from about 1:1 to about 1.5:1. The coupling reaction is carried out in the presence of 1-(3-dimethylaminopropyl)-3-ethylcarbodiimide hydrochloride (WSC) or dicyclohexylcarbodiimide (DCC) and 1-hydroxybenzotriazole (HOBT) in the presence of N-methylmorpholine (NMM), employing a molar ratio of WSC or DCC:XII of within the range of from about 1:1 to about 3:1, preferably from about 1:1 to about 1.5:1. The HOBT will be employed in a molar ratio to WSC or DCC of within the range of from about 1:1 to about 3:1, preferably from about 1:1 to about 1.5:1 while the NMM will be employed in a molar ratio to HOBT of within the range of from about 2:1 to about 5:1, preferably from about 2:1 to about 3:1. The above reaction will be carried out at a temperature within the range of from about −20° C. to about 40° C. and preferably from about 0° C. to about 25° C.

Alternatively, acid XII may be activated by forming a mixed anhydride, mixed carbonate, or preferably acid chloride (by known literature methods), using a slight excess (of from about 10 to about 50%) of amine and acid scavenger relative to the acid chloride. A reaction temperature of from about −78° C. to about 0° C. will be employed.

The term lower alkyl or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent, or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, and/or alkoxy groups.

The term "aryl" or "Ar" as employed herein refers to monocyclic or bicyclic aromatic groups containing from 6 to 10 carbons in the ring portion, such as phenyl or naphthyl. Aryl (or Ar) phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), alkylsulfonyl, and/or arylsulfonyl.

The term "alkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or 'halo' as used herein refers to Cl, Br, F or I, with Cl preferred.

The compounds prepared by the method of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds prepared by the method of the invention, namely, cis-exo, cis-endo and all trans forms and stereoisomeric pairs may be prepared by employing starting materials and following the procedures as outlined in U.S. Pat. No. 4,143,054 and are fully disclosed in U.S. Pat. No. 5,100,889 which is incorporated herein by reference.

The nucleus in each of the compounds prepared by the method of the invention is depicted as

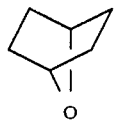

for matter of convenience; it will also be appreciated that the nucleus in the compounds of the invention may be depicted as

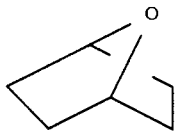

The compounds prepared by the method of this invention are thromboxane receptor antagonists and as such are useful as inhibitors of thromboxane receptor mediated actions. The term "thromboxane receptor antagonist" includes compounds which are so-called thromboxane $A^2$ receptor antagonists, thromboxane $A^2$ antagonists, thromboxane $A^2$/prostaglandin endoperoxide antagonists, TP-receptor antagonists, or thromboxane antagonists.

The compounds prepared by the method of the invention are also thromboxane synthetase inhibitors and thus are useful as inhibitors of thromboxane production.

Examples of various utilities of the compounds prepared by the method of the invention are set out in U.S. Pat. No. 5,100,889.

The following Examples represent preferred embodiments of the present invention. Unless otherwise indicated, all temperatures are expressed in degrees Centigrade.

EXAMPLE 1

[1S-(1α,2α,3α,4α)]-2-[[3-[5-Bromo-4-(pentylamino)carbonyl]-2-oxazolyl]-7-oxabicyclo[2.2.1]hept-2-yl]methyl]benzenepropanoic acid, methyl ester

A.
N-Pentyl-N2-[(phenylmethoxy)carbonyl]-L-serinamide

A 5-L, 3-necked flask was charged with N-CBZ-L-serine (110 g, 0.46 mole) (CBZ =carbobenzyloxy) followed by dichloromethane (2.1 L). The resulting slurry was stirred under argon and treated with triethylamine (61.7 mL, 0.443 mole) over several minutes. The resulting hazy solution was cooled to an internal temperature of −35° and treated over 10 minutes with trimethylacetylchloride (51.06 mL, 0.415 mole) such that the internal temperature did not rise above −30°. The reaction was stirred an additional 40 minutes at −25° to −30°, treated with pyridine (35.2 mL, 0.435 mole) over 5 minutes and stirred an additional 10 minutes. Amylamine (51 mL, 0.44 mole) was added over 10 minutes while maintaining the internal temperature at −25° to −29°. The reaction was stirred for 30 minutes while warming to −25°. A precipitate formed during this warming. The reaction was further warmed to −10° over 40 minutes during which time the precipitate redissolved. After stirring an additional 20 minutes at −10°, the reaction was quenched by the addition of 500 mL of 1N HCl. The biphasic mixture was stirred for 20 minutes and transferred to a separatory funnel. The aqueous layer was extracted with dichloromethane (2×75 mL). The combined dichloromethane solutions were concentrated in vacuo to a weight of 500 g. Ethyl acetate (EtOAc) (2.25 L) was added and the organic solution was washed with 1N HCl (2×400 mL) and 1N $K_2CO_3$ (1×700 mL and 2×500 mL). The organic solution was dried (magnesium sulfate), filtered and concentrated in vacuo to the title compound which was used in the next step without purification.

B. N-Pentyl-L-serinamide, 1:1 oxalate salt

The Part A compound was evaporated from 95% ethanol (EtOH) to remove residual solvents. The residue was dissolved in 95% EtOH (1.28 L) and treated under nitrogen with 20% Pd(OH)$_2$ (12.8 g). The mixture was stirred and sparged with hydrogen. After 2.5 hours the catalyst was filtered off and washed with 95% EtOH. The filtrate was concentrated in vacuo to 73.1 g. A portion of this material (36.3 g, 0.21 mole) was redissolved in 95% EtOH (221 mL) and added slowly to a stirred room temperature solution of oxalic acid dihydrate (31.5 g, 0.25 mole) in 95% EtOH (221 mL). After the addition the resulting slurry was further diluted with 120 mL of 95% EtOH, stirred an additional 30 minutes and then heated to reflux. The slurry was treated with water (29 mL) to afford a clear, light yellow solution. After stirring an additional 40 minutes the heat was removed and the solution cooled. The resulting slurry was stirred at ambient temperature for 18 hours, filtered and washed with 95% EtOH (1×72 mL, and 1×48 mL) and hexane (2×48 mL). Drying in vacuo produced 42.9 g (77.3%) of the title compound, mp 174° C.

C.
[1S-[1α,2α,3α,4α]]-2-[[3-[[[1-(Hydroxymethyl)-2-oxo-2-pentylamino)ethyl]amino]carbonyl]-7-oxabicyclo[2.2.1-]hept-2-yl]methyl]benzenepropanoic acid, methyl ester To a stirred solution of [1S-(1α,2α,3α,4α)]-2-[(3-carboxy-7-oxabicyclo[2.2.1]hept-2-yl)methyl]benzenepropanoic acid, methyl ester (prepared as described in U.S. Pat. No. 5,100,889) (17.6 g, 55.3 mmol) and 4-methylmorpholine (12.2 mL, 111 mmol) in 100 mL of DMF under argon at −10° C. was added dropwise isobutylchloroformate (7.94 mL, 61.2 mmol) over a 15 minute period. This solution was stirred at −10° C. for 50 minutes at which time n-pentyl-L-serinamide (10.6 g, 57.5 mmol) was added. The reaction mixture was stirred at −10° C. for 1 hour and at room temperature for 16 hours. This mixture was diluted with 2 L of ethyl acetate (EtOAc) and washed with 1N HCl solution (2×600 mL), saturated NaHCO$_3$ solution (1×600 mL) and brine (1×600 mL). The EtOAc layer was dried (MgSO$_4$), filtered and concentrated in vacuo. This was triturated in 600 mL of 1:1 etherhexane to give 25.2 g (96%) of title amide.

TLC: silica gel, 4% CH$_3$OH/CH$_2$Cl$_2$, R$_f$ 0.38, Cerium dip

C$^1$. Alternative Procedure for Forming C.

A solution of Part C acid ester starting material (30.27 g, 95.06 mmol) and DMF (1.5 mL, 19.37 mmol) in CH$_2$Cl$_2$ (200 mL) was cooled to an internal temperature of 0° C. under an argon atmosphere. To the above solution was added oxalyl chloride (9.1 mL, 104.57 mmol) over ~2.5 minutes. After 2 hours, gas evolution had ceased. A 75 μL aliquot was removed and quenched into MeOH. TLC analysis of this solution showed no remaining starting acid, thus indicating complete conversion to the acid chloride. Toluene (30 mL) was added to the reaction mixture. The crude acid chloride solution was partially concentrated to an oil/solid mixture (43.37 g).

In a separate flask, a suspension of N-pentyl-L-serinamide oxalate salt (30.26 g, 114.50 mmol) in CH$_2$Cl$_2$ (200 mL was treated sequentially, under argon, with DBU (33.4 mL, 223.28 mmol) and Et$_3$N (16.0 mL, 114.50 mmol). The resulting solution was cooled to −78° C. The crude acid chloride was redissolved in CH$_2$Cl$_2$ (350 mL), cooled to 8° C. under argon, and added to the solution of the amine via cannula such that the reaction temperature never exceeded −72° C. The addition process required 35 minutes. The flask containing the acid chloride solution was rinsed with CH$_2$Cl$_2$ (30 mL) which was transferred to the reaction mixture. After 45 minutes an aliquot was removed and quenched into MeOH. TLC analysis of the solution showed no evidence of unreacted acid chloride; only Part C title compound and a trace of starting acid were present. The dry ice/acetone bath was removed and with vigorous stirring, 1N HCl (500 mL) was immediately added. The internal temperature quickly rose to −10° C. After transferring to a separatory funnel, additional water (1 L) and CH$_2$Cl$_2$ (250 mL) were added. The layers were mixed and split. The aqueous layer was extracted with CH$_2$Cl$_2$ (250 mL). The organic phases were combined and washed with 1N HCl 250 mL) and saturated aqueous NaHCO$_3$ (500 mL). The aqueous NaHCO$_3$ solution was back-extracted with CH$_2$Cl$_2$ (250 mL). The organic solutions were combined, washed again with saturated aqueous NaHCO$_3$ (250 mL) and saturated aqueous NaCl (500 mL), dried (MgSO$_4$), filtered, concentrated, and left under high vacuum for 12 hours to give the crude title compound (44.27 g).

A portion of this material (38.27 g) was placed in a flask with water (7.25 mL) and EtOAc (344 mL) and the mixture was brought to a boil. The resulting clear yellow solution was allowed to cool to room temperature and stand for 22 hours. EtOAc (125 mL) was added to slurry the all-engulfing white solid and the crystals were recovered via filtration. The white crystals were washed sequentially with EtOAc (2×75 mL) and hexanes (1×200 mL), air dried (1.5 hours), and placed under high vacuum for 24 hours to give the title compound (33.87 g).

Procedure I for D. and E.

D.

[1S-[1α,2α,3α(R*),4α]]-2-[[3-[[[1-[Methylsulfonyl)oxymethyl]-2-oxo-2-(pentylamino)ethyl]amino]carbonyl]-7-oxabicyclo[2.2.1]hept-2-yl]methyl]benzenepropanoic acid, methyl ester and

E.

[1S-[1α,2α,3α(R*),4α]]-2-[[3-[[[1-(Chloromethyl)-2-oxo-2-(pentylamino)ethyl]amino]carbonyl]-7-oxabicyclo[2.2.1]hept-2-yl]methyl]benzenepropanoic acid, methyl ester To a stirred solution of Part C amide (25.2 g, 53.2 mmol) in 480 mL of dry CHCl$_2$ at −10° C. under argon was added, in order, triethylamine (Et$_3$N) (8.88 mL, 63.8 mmol) and methanesulfonyl chloride (4.53 mL, 58.5 mmol). This solution was stirred at −10° C. for 15 minutes and diluted with 200 mL of CH$_2$Cl$_2$. This mixture was washed with ice-cold 1N HCl solution (2×150 mL) and a 1:1 mixture of saturated NaHCO$_3$ solution and brine (1×150 mL). The organic layer was dried (MgSO$_4$), filtered and concentrated in vacuo to give solid intermediate Part D mesylate. To a stirred solution of this Part D mesylate in 120 mL of DMF was added anhydrous lithium chloride (5.58 g, 133 mmol). An exotherm was noted. This solution was stirred at room temperature for 18 hours and then diluted with 1 L of CH$_2$Cl$_2$. The solution was washed with 10% LiCl solution (2×250 mL), water (2×250 mL), saturated NaHCO$_3$ solution (1×250 mL) and brine (1×250 mL). The organic layer was dried (MgSO$_4$), filtered and concentrated in vacuo to give Part E chloride (26.2 g, 100% crude yield).

TLC: silica gel, 3:1 EtOAc-hexane, R$_f$ 0.72, cerium dip mp 180°-182° C.

[α]$_D$= −5.5° (c=0.9, CHCl$_3$).

Anal. Calc'd for C$_{26}$H$_{37}$N$_2$O$_5$Cl: C, 63.34; H, 7.56; N, 5.68; Cl, 7.19, Found: C, 63.39; H, 7.68; N, 5.69; Cl, 7.36.

Alternative Procedure II for D. and E.

To a stirred solution of Part C amide (25.2 g, 53.2 mmol) in 250 mL of dry CH$_2$Cl$_2$ at −10° C. under argon is added, in order, triethylamine (Et$_3$N) (8.88 mL, 63.8 mmol) and methanesulfonyl chloride (4.53 mL, 58.5 mmol). This solution is stirred at −10° C. for 15 minutes and diluted with 100 mL of DMF. To this mixture is added anhydrous lithium chloride (5.58 g, 133 mmol) in 50 mL DMF. This solution is stirred at room temperature for 18 hours and then diluted with 1 L of CH$_2$Cl$_2$. The solution is washed with 10% LiCl solution (2×250 mL), water (2×250 mL), saturated NaHCO$_3$ solution (1×250 mL) and brine (1×250 mL). The organic layer is dried (MgSO$_4$), filtered and concentrated in vacuo to give Part E chloride.

Alternative Procedure III for D. and E.

To a stirred solution of Part C amide (25.2 g, 53.2 mmol) in 350 mL of dry CH$_2$Cl$_2$ at −10° C. under argon is added, in order, triethylamine (Et$_3$N) (8.88 mL, 63.8 mmol) and methanesulfonyl chloride (4.53 mL, 58.5 mmol). This solution is stirred at −10° C. for 15 minutes and diluted with 200 mL of CH$_2$Cl$_2$. This mixture is washed with ice-cold 1N HCl solution (2×150 mL) and a 1:1 mixture of saturated NaHCO$_3$ solution and brine (1×150 mL). The organic layer is dried (MgSO$_4$), filtered and concentrated in vacuo to give solid intermediate Part D mesylate. To a stirred solution of this Part D mesylate in 250 mL of $CH_2Cl_2$ portionwise is added benzyltributylammonium chloride (33 g, 107 mmol). This solution is stirred at room temperature for 18 hours and then diluted with 1 L of $CH_2Cl_2$. The solution is washed with 10% LiCl solution (2×250 mL), water (2×250 mL), saturated (1×250 mL) and brine (1×250 mL). The $NaHCO_3$ solution (1×250 mL) and brine (1×250 mL). The organic layer is dried ($MgSO_4$), filtered and concentrated in vacuo to give Part E chloride.

F.
[1S-[1α,2α,3α(R*),4α]]-2-[[3-[[[1-Methylene-2-oxo-2-(pentylamino)ethyl]amino]carbonyl]-7-oxabicyclo[2.2.1]hept-2-yl]methyl]benzenepropanoic acid, methyl ester To a stirred solution of Part E chloride (26.2 g, 53.2 mmol) in 740 mL of dry $CH_2Cl_2$ under argon was added DBU (15.0 mL, 106 mmol). The reaction mixture was stirred at room temperature for 4.5 hours and washed with 1N HCl solution (2×400 mL), half-saturated $NaHCO_3$ solution (1×400 mL) and brine (1×400 mL). The organic layer was dried ($MgSO_4$), filtered and concentrated in vacuo to give 26 g of crude oil. This crude oil (25 g) was chromatographed on 900 g of Merck silica gel K-60 using 2 L of 40% EtOAc in hexane and 6 L of 50% EtOAc in hexane as eluants to give 17.4 g (72%) of title olefin as a viscous oil.

$[\alpha]_D = +27.7°$ (c=1.0, $CH_3OH$).

TLC silica gel, 2:1 EtOAc-hexane, $R_f$ 0.64, cerium dip.

Anal. Calc'd for $C_{26}H_{36}N_2O_5$: C, 68.40; H, 7.95; N, 6.14, Found: C, 68.10; H, 8.12; N, 5.87.

This olefin was stored at −78° C. under argon.

G.
[1S-[1α,2α,3α(R*,Z),4α]]-2-[[3-[[[1-(Bromomethylene)-2-oxo-2-(pentylamino)ethyl]amino]carbonyl]-7-oxabicyclo[2.2.1]hept-2-yl]methyl]benzenepropanoic acid, methyl ester and

H.
[1S-[1α,2α,3α(R*,E),4α]]-2-[[3-[[[1-(Bromomethylene)-2-oxo-2-(pentylamino)ethyl]-amino]carbonyl-7-oxabicyclo[2.2.1]hept-2-yl]methyl]benzenepropanoic acid, methyl ester To a stirred solution of purified Part F olefin (13.8 g, 30.3 mmol) in 500 mL of dry $CH_2Cl_2$ under argon at −78° C. was added bromine (1.58 mL, 30.7 mmol). At the end of the addition of bromine the reaction mixture became bright yellow. This yellow solution was stirred at −78° C. for 15 minutes and treated slowly with triethylamine (16.8 mL, 121 mmol). The reaction flask was then transferred to a wet ice bath and stirred for 40 minutes. The mixture was diluted with 200 mL of $CH_2Cl_2$ and washed with 2% $NaHSO_3$ solution (2×250 mL), water (1×250 mL) and brine (1×250 mL). The organic layer was dried ($MgSO_4$), filtered and concentrated in vacuo. This was triturated with 1 L of 3:7 hexane-ether to give 14.9 g (92% or 66% from starting methyl ester used in Part C) of 9:1 mixture of title vinyl bromides G (major) and H (minor).

TLC: silica gel, 1:2 hexane-EtOAc, $R_f$, 0.31, 0.56, UV & cerium dip.

HPLC: $R_T$=6.3 minutes (87%) and 7.2 minutes (9.5%), linear gradient of 72-90% aqueous methanol containing 0.2% $H_3PO_4$, 20 minutes, detected at 217 nm, YMC S-3 (ODS), 6.0×150 mm, 3 micron spherical end capped column, flow rate 1.5 mL/minute.

The product from a smaller scale reaction (1.9 mmol) was purified and separated by chromatography on silica gel (150 mL, Merck), eluting with ethyl acetate:hexane (1:1 and 1:2) and finally with ethyl acetate to give the two isomers G and H. The minor isomer H was obtained as a white solid (94 mg, 9.2%). mp 104°-108° C.

$[\alpha]_D = +46.0°$ (c=0.7, $CHCl_3$).

Anal. Calc'd for $C_{26}H_{35}N_2O_5Br$: C, 58.32; H, 6.59; N, 5.23, Br, 14.92. Found: C, 58.18; H, 6.66; N, 4.99; Br, 15.14.

The major isomer G was also a white solid (877 mg, 86%). mp 160°-164° C.

$[\alpha]_D = -37.9°$ (c=1.0 $CHCl_3$).

Anal. Calc'd for $C_{236}H_{35}N_2O_5Br$: C, 58.32; H, 6.59; N, 5.23, Br, 14.92. Found: C, 58.28; H, 6.64; N, 4.96; Br, 15.19.

Alternate G and H preparation

To a stirred solution of crude Part E olefin (olefin was worked up as described in the above preparation and used without purification by column chromatography, 1.10 g) in 42 mL of dry $CH_2Cl_2$ under argon at −78° C. was added bromine over 10 minutes. Bromine was added until a bright yellow color appeared and stayed in the reaction mixture. The amount of bromine used in this scale was 125 μL. The mixture was stirred at −78° C. for 5 minutes and treated with $Et_3N$ (1.33 mL, 9.60 mmol). The reaction flask was then moved to a wet-ice bath and stirred for 30 minutes. The mixture was diluted with 100 mL of $CH_2Cl_2$ and washed with 2% $NaHSO_3$ solution (2×60 mL), water (1×60 mL) and brine (1×60 mL). The organic layer was dried ($MgSO_4$), filtered and concentrated in vacuo. This was triturated in 50 mL of ether to give 716 mg (57% from starting acids used in Part C) of a 9:1 mixture of vinyl bromides G and H.

TLC: silica gel 1:2 hexane-EtOAc, $R_f$, Part G compound, 0.31, Part H compound, 0.56, cerium dip.

TLC of the mother liquor indicated that the vinyl bromides were the major components in this mixture.

I.
[1S-(1α,2α,3α,4α)]-2-[[3-[5-Bromo-4-[(pentylamino)carbonyl]-2-oxazolyl]-7-oxabicyclo[2.2.1]hept-2-yl]methyl]benzenepropanoic acid, methyl ester A suspension of $CuBr_2$ (0.89 g, 4 mmol) and DBU (1.2 mL, 8 mmol) in 20 mL deoxygenated $CH_2Cl_2$ was stirred mechanically at room temperature under argon for 10 minutes. A slurry of the mixture of Part G and Part H vinyl-bromides diamides (1.078 g, 2 mmol) in 5 mL $CH_2Cl_2$ was added to the solution of the cupric bromide. After stirring for 8 hours, a second batch of reagents, DBU (1.2 mL, 8 mmol) and $CuBr_2$ (0.89 g, 4 mmol), was added. After 24 hours the solvent was removed and dark brown oil was treated with 40 mL of a mixture of saturated aqueous $NH_4Cl$/conc. $NH_4OH$ (2:1, pH ~10) and 50 mL EtOAc. The light orange organic layer was separated and the blue aqueous layer was extracted with EtOAc (3×50 mL). The combined organic extracts were washed with a mixture of saturated aqueous $NH_4Cl$/conc. $NH_4OH$ (2:1, 3×30 mL) and 10% aqueous citric acid (3×30 mL). The organic extract was washed further with aqueous $NaHCO_3$ and brine and then dried ($MgSO_4$). The solution was stirred with charcoal (activated carbon, Darco) for 25 minutes and then filtered through a pad of MgSO4. The filtrate was evaporated to give 0.866 g (yield 81%) of title compound. The product was purified by flash column chromatography over silica gel (150 mL). The column was eluted with a 1:1 mixture of EtOAc/hexane (1:2) and 25 mL fractions were collected. TLC homogeneous fractions 3 to 21 were combined and evaporated. The residue was dissolved in 10 mL CH2Cl2 and evaporated again to remove EtOAc. The residue was dried under vacuum to furnish 0.7 g (yield 65%) title compound as a colorless viscous oil.

$[\alpha]_D = +19.5°$ (c=1, CHCl3).

Anal. Calc'd for $C_{26}H_{33}BrN_2O_5$ (MW 533.47): C, 58.54; H, 6.24; N, 5.25; Br, 14.98, Found: C, 58.77; H, 6.23; N, 5.25; Br, 14.99.

EXAMPLE 2

[1S-(1α,2α,3α,4α)]-2-[[3-[5-Bromo-4-[(pentylamino)-carbonyl]-2-oxazolyl]-7-oxabicyclo[2.2.1]hept-2-yl]methyl]benzenepropanoic acid, methyl ester

A.

[1S-[1α,2α,3α,4α]]-2-[[3-[[[1,1-(Dibromomethylene)-2-oxo-2-(pentylamino)ethyl]amino]carbonyl]-7-oxabicyclo[2.2.1]hept-2-yl]methyl]benzenepropanoic acid, methyl ester A solution of Example 1 Part G and H vinylbromides (0.503 g, 0.94 mmol) in 20 ml dry methylene chloride was cooled to −78°. Bromine (0.048 ml, 0.94 mmol) was added to the solution and after 30 minutes additional bromine (0.01 ml, 0.2 mmol) was introduced into the reaction mixture. After 20 minutes triethyl amine (0.52 ml, 3.78 mmol) was added via syringe and stirring was continued for 20 minutes. The mixture was poured into 60 ml aqueous saturated sodium bisulphide and extracted with 50 ml dichloromethane. The organic solution was washed with 30 ml brine, dried over potassium carbonate, filtered and solvent was evaporated to give 0.545 g (yield 94.4%) of title compound. TLC: silica gel, EtOAc/hexane 3:1, $R_f$ of title vinyldibromide 0.28, visualized by UV and ceric sulphate/ammonium molybdate.

B.

[1S-(1α,2α,3α,4α)]-2-[[3-[5-Bromo-4-[(pentylamino)-carbonyl]-2-oxazolyl]-7-oxabicyclo[2.2.1]hept-2-yl]methyl]benzenepropanoic acid, methyl ester A suspension of cupric bromide (CuBr2) (0.054 g, 0.24 mmol) and 1,8-diazabicyclo[5.4.0]undec-7-ene (DBU) (0.072 ml, 0.48 mmol) in 1.8 ml deoxygenated dry methylene chloride (CH2Cl2) was stirred at room temperature under argon for 10 min. Solid Part A vinyldibromide diamide (0.074 g, 0.12 mmol) was added to the solution of the oxidation reagent. The reaction was complete after stirring for 20 hours (TLC: Silica gel, ethyl acetate (EtOAc)/hexane (3:1), $R_f$ of bromooxazole=0.57, dibromide 0.32, visualized by UV and ceric sulphate, ammonium molybdate). The solvent was removed and dark brown oil was treated with 10 ml ethyl acetate (EtOAc) and 7 ml of a mixture of saturated aq. ammonium chloride (NH4Cl)/conc. ammonium hydroxide (NH4OH) (2:1, pH ~10). The light orange organic layer was separated and the blue aq. layer was extracted with ethyl acetate (EtOAc) (3×4 ml). The combined organic extracts were washed with a mixture of saturated ammonium chloride (NH4Cl)/conc. ammonium hydroxide (NH4OH) (2:1, 3×5 ml) and 10% aq. citric acid (3×5 ml). The organic extract was washed further with aq. sodium bicarbonate (NaHCO3) and brine and then dried magnesium sulphate (MgSO4). The solution was stirred with charcoal (activated carbon, Darco) for 25 min. and then filtered through a pad of magnesium sulphate (MgSO4). The filtrate was evaporated to give 0.051 g (yield ~80%) of the title compound.

EXAMPLE 3

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, methyl ester (Hydrogenolysis of Example 1 bromooxazole to the corresponding oxazole).

A solution of Example 1 bromooxazole (0.085 g, 0.16 mmol) in ethanol (1 ml) and methanol (2 ml) was stirred under argon and 10% Pd-C (0.03 g) was added. The mixture was stirred under hydrogen (in a balloon) for 24 hours. TLC (silica gel, ethylacetate/hexane (3:1), $R_f$ of bromooxazole=0.57, oxazole 0.42, visualized by UV and ceric sulphate, ammonium molybdate) showed no starting material. The mixture was filtered through Celite and solvent was evaporated to give 0.058 g (~80% crude yield) of the title compound.

EXAMPLE 4

[1S-(1α,2α,3α,4α)-2-[[3-[4-[(Pentylamino)carbonyl]-2-oxazolyl]-7-oxabicyclo[2.2.1]hept-2-yl]methyl]benzenepropanoic acid Aqueous 1N NaOH (5 mL) was added to a solution of Example 3 compound (0.912 g, 2 mmol) in THF (10 mL) and the reaction mixture was stirred under argon. After 4.5 hours, the mixture was evaporated under vacuum to ~5 mL and diluted with 10 mL water. HCl (1N, 2.8 mL) was added to the aqueous solution and its pH was adjusted to ~8.5 with a few drops of aqueous NaHCO3. The solution was washed with EtOAc (15 mL), CH2Cl2 (10 mL) and EtOAc (15 mL). The aqueous layer was separated and acidified with 1N HCl to pH 6.5. The product was extracted with EtOAc (150 mL) and CH2Cl2 (50 mL). Organic extracts were combined, dried (MgSO4) and evaporated to give a white solid. The product was dried under vacuum overnight to furnish 0.808 g (yield 92%) of title acid, mp 157°–59°, $[\alpha]_D = +57.5°$ (c=1, CHCl3).

Anal. Calc'd for $C_{25}H_{32}N_2O_5$ (MW 440.54): C, 68.16; H, 7.32; N, 6.36; H20, 0.0, Found: C, 67.99; H, 7.06; N, 6.33; H20, 0.0 (KF).

EXAMPLE 5

[1S-(1α,2α,3α,4α)]-2-[[3-[5-Bromo-4-[(pentylamino)-carbonyl]-2-oxazolyl]-7-oxabicyclo[2.2.1]hept-2-yl]methyl]benzenepropanoic acid A. Purification of [1S-(1α,2α,3α,4α)]-2-[[3-[5-Bromo-4-[(pentylamino)-carbonyl]-2-oxazolyl]-7-oxabicyclo[2.2.1]hept-2-yl]methyl]benzenepropanoic acid, methyl ester Example 1 compound (prepared as a by-product as described in Example 2 Part A(1) in U.S. application Ser. No. 900,384, filed June 18, 1992) (2 g) was rechromatographed over flash silica gel (K-60, 400 mL, in a 50 mm. dia. column). The column was eluted with 2 1 of 50% EtOAc/hexane and 35 mL fractions were collected. Fractions 14 to 18 gave 1.14 g Example 3 product which still contained impurities. The product was rechromatographed over 200 mL flash silica gel. The column was eluted successively with 1L 10% EtOAc in hexane, 1L 20% EtOAc in hexane and 2L 30% EtOAc in hexane collecting 35 mL fractions. Fractions 60 to 75 were combined and evaporated to give 0.91 g purified title compound as a viscous oil.

B. Saponification of Part A compound to Example 5 compound
([1S-(1α,2α,3α,4α)]-2-[[3-[5-Bromo-4-[(pentylamino)-carbonyl]-2-oxazolyl]-7-oxabicyclo[2.2.1]hept-2-yl]methyl]-benzenepropanoic acid)

Aqueous 1N NaOH (2 mL) was added to a solution of purified Part A compound (0.406 g, 0.76 mmol) in 4 mL THF. The biphasic mixture was stirred under argon at room temperature. After 3.5 hours THF was removed on a rotary evaporator and the aqueous solution (~10 mL) was extracted twice with 3 mL t-BuOMe. The aqueous solution was acidified with 1N HCl to pH 8.5 and 10 mL EtOAc was added before further acidification to pH 6. The organic layer was separated and the aqueous layer was extracted with EtOAc (2×4 mL). The combined organic extracts were washed with brine, dried (MgSO$_4$) and the solvent was removed under vacuum to give 0.54 g of a snow-white solid. Crude product (0.5 g) was triturated with 5 mL t-BuOMe. The insoluble solid was filtered and dried under vacuum over P$_2$O$_5$ to give 0.37 g (yield 95%) of title compound; mp 153°–55°.

$[\alpha]_D = +24.8°$ (c=1, CHCl$_3$).

Anal. Calc'd for C$_{25}$H$_{31}$BrNO$_5$ (MW 519.44): C, 57.81; H, 6.02; N, 5.39; Br, 15.38; H$_2$O, 0.0, Found: C, 58.23; H, 5.94; N, 5.08; Br, 15.39; H$_2$O, 0.0 (KF via desorption).

C. Recrystallization of [1S-(1α,2α,3α,4α)]-2-[[3-[5-Bromo-4-[(pentylamino)-carbonyl]-2-oxazolyl]-7-oxabicyclo[2.2.1]hept-2-yl]methyl]-benzenepropanoic acid Part B Bromoacid (0.32 g) was dissolved in 20 mL hot t-BuOMe and filtered through a filter paper. The solution was seeded with crystals of Example 5 compound at room temperature and let stand with a loose stopper. After 2 days birefringent crystals (long thin rods) were separated from the solvent by decantation, washed with t-BuOMe and dried under vacuum to give 0.136 g (40.3% yield first crop Example 5 compound); mp 153°–55° dec.

Anal. Calc'd for C$_{25}$H$_{31}$BrN$_2$O$_5$ (MW 519.44): C, 57.81; H, 6.02; N, 5.39; Br, 15.38, Found: C, 57.97; H, 6.05; N, 5.25; Br, 15.53.

EXAMPLE 6

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid (Hydrogenolysis of Example 5 bromooxazole acid to corresponding oxazole (Example 6)).

Example 5 bromooxazole acid (0.052 g, 0.1 mmol) was added to a solution of sodium bicarbonate (0.021 g, 0.25 mmol) in 1 ml water. The solution was diluted with ethanol (0.5 ml) and dimethylformamide (0.5 ml). 5% Pd-C (0.026 g) was added and hydrogen gas was bubbled through the stirred suspension for 3 hours. TLC (silica gel, ethyl acetate (EtOAc)/hexane 3:1, R$_f$ of starting material bromooxazole acid= 0.71, product oxazole acid 0.61, visualized by UV and ceric sulphate, ammonium molybdate) showed no starting material. The mixture was filtered and solvent was removed completely under vacuum. The colorless residue was redissolved in water (5 ml) and the solution was acidified with a few drops of 1N HCl to pH 4 to give a white precipitate. The mixture was extracted with ethyl acetate (EtOAc) (3×5 ml) and the organic extracts were washed with water (3×5 ml), brine (5 ml). The solution was dried, magnesium sulphate (MgSO$_4$) and solvent was evaporated to give 0.044 g (yield 100%) of the title compound as a white solid. mp 141°–143° C. Proton NMR (270 MHz, CDCl$_3$) of this product was identical to an authentic sample of the title compound. Solvent was removed from the NMR sample and the residue was once evaporated from 2 ml chloroform.

Anal. Calc'd for C$_{25}$H$_{32}$N$_2$O$_5$·0.06 H$_2$O·0.07 CHCl$_3$; MW 440.54/449.98: C 6.92, H 7.21, N 6.23; Found: C 6.69, H 7.23, N 6.24.

EXAMPLE 7

[1S-(1α,2α,3α,4α)]-2-[[3-[5-Bromo-4-[(pentylamino)-carbonyl]-2-oxazolyl]-7-oxabicyclo[2.2.1]hept-2-yl]methyl]benzenepropanoic acid, methyl ester (Cyclization of Example 1 Part F Vinyldiamide to Bromooxazole)

A suspension of cupric bromide (CuBr$_2$) (0.196 g, 0.88 mmol) and 1,8-diazabicyclo[5.4.0]-undec-7-ene (DBU) (0.263 ml, 1.76 mmol) in 1.1 ml deoxygenated dry methylene chloride (CH$_2$Cl$_2$) was stirred at room temperature under argon for 10 min. Solid Example 1 Part F vinyldiamide (0.1 g, 0.22 mmol) was added to the solution of the cupric bromide. The reaction was complete after stirring for 20 hours (TLC: Silica gel, ethyl acetate/hexane (3:1), R$_f$ of bromooxazole =0.59, dibromide 0.35, visualized by UV and ceric sulphate, ammonium molybdate). Ethyl acetate (10 ml) was added and the mixture was washed with a mixture of saturated aq. ammonium chloride /conc. ammonium hydroxide (3:1). The light orange organic layer was separated and the blue aq. layer was extracted with ethyl acetate. The combined organic extracts were washed with a mixture of saturated ammonium chloride/conc. ammonium hydroxide (3:1) and 10% aq. citric acid (3×5 ml). The organic extract was washed further with aq. sodium bicarbonate and brine and then dried (magnesium sulphate). The solution was stirred with charcoal (activated carbon, Darco) for 25 min. The mixture was filtered and the filtrate was evaporated to give the crude product title compound which also contained 20% Example 3 oxazole by NMR.

What is claimed is:

1. A method for preparing a bromooxazole of the structure

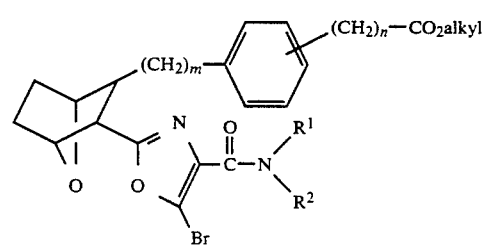

wherein
m is 1, 2 or 3;
n is 0, 1, 2, 3 or 4;

R$^1$ is hydrogen, lower alkyl, aryl, aralkyl, cycloalkyl, cycloalkylalkyl, or an amide of the structure $$-(CH_2)_t-\overset{O}{\overset{\|}{C}}-\overset{H}{\overset{|}{N}}-Ra \quad \text{or} \quad -(CH_2)_t-\overset{H}{\overset{|}{N}}-\overset{O}{\overset{\|}{C}}-Ra$$

wherein t is 1 to 12 and Ra is lower alkyl, aryl, cycloalkyl or cycloalkylalkyl;

R$^2$ is hydrogen, lower alkyl, aryl, or aralkyl; or

R$^1$ and R$^2$ together with the N to which they are linked form a 5- to 8-membered ring which has only the single N heteroatom, wherein the term "aryl" by itself or as part of another group is phenyl or naphthyl, or phenyl or naphthyl optionally substituted with 1 or 2 substituents which are lower alkyl, trifluoromethyl, halogen, alkylsulfonyl and/or arylsulfonyl, which comprises providing a vinyl compound of the structure wherein X$^1$ and X$^2$ are the same or different and are H or Br, treating the above vinyl compound with a metal halide wherein the metal is ferric, cupric or cuprous, and a base which is 1,8-diazabicyclo[5.4.0]-undec-7-ene (DBU) or 1,5-diazabicyclo-[4.3.0]non-5-ene (DBN), to convert said vinyl compound to the bromooxazole.

2. The method as defined in claim 1 wherein R$^1$ is hydrogen, R$^2$ is lower alkyl, m is 1 and n is 2.

3. The method as defined in claim 1 wherein R$^2$ is pentyl.

4. The method as defined in claim 2 wherein m is 1, n is 2, R$^1$ is H, R$^2$ is pentyl and CO$_2$alkyl is CO$_2$CH$_3$.

5. The method as defied in claim 1 wherein the metal halide is cupric bromide, cuprous bromide or ferric bromide, and the base is DBU.

6. The method as defined in claim 1 where in the vinyl compound starting material one of X$^1$ and X$^2$ is H and the other is Br.

7. The method as defined in claim 1 where in the vinyl compound starting material X$^1$ is Br and X$^2$ is Br.

8. The method as defined in claim 1 where in the vinyl starting material is

9. The method as defined in claim 1 where in the vinyl starting material is

10. The method as defined in claim 1 wherein the reaction is carried out in the presence of an inert organic solvent which is dichloromethane.

11. The method as defined in claim 1 wherein the metal halide is copper bromide.

12. The method as defined in claim 1 wherein the cupric bromide is employed in a molar ratio to vinyl starting material of within the range of from about 2.5:1 to about 5:1, and the base is employed in a molar ratio to vinyl starting material of within the range of from about 2.5:1 to about 5:1.

13. A method for preparing an oxazole acid of the structure wherein m is 1, 2 or 3;

n is 0, 1, 2, 3 or 4;

R$^1$ is hydrogen, lower alkyl, aryl, aralkyl, cycloalkyl, cycloalkylalkyl, or an amide of the structure $$-(CH_2)_t-\overset{O}{\overset{\|}{C}}-\overset{H}{\overset{|}{N}}-Ra \quad \text{or} \quad -(CH_2)_t-\overset{H}{\overset{|}{N}}-\overset{O}{\overset{\|}{C}}-Ra$$

wherein t is 1 to 12 and Ra is lower alkyl, aryl, cycloalkyl or cycloalkylalkyl;

R$^2$ is hydrogen, lower alkyl, aryl, or aralkyl; or

R$^1$ and R$^2$ together with the N to which they are linked form a 5- to 8-membered ring which has only the single N heteroatom, wherein the term "aryl" by itself or as part of another group is phenyl or naphthyl, or phenyl or naphthyl optionally substituted with 1 or 2 substituents which are lower alkyl, trifluoromethyl, halogen, alkylsulfonyl and/or arylsulfonyl; which comprises providing a vinyl compound of the structure

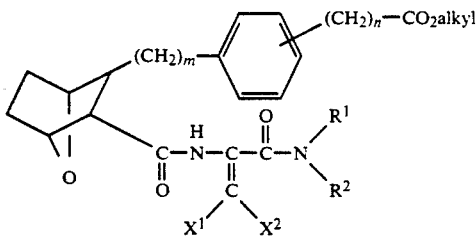

wherein $X^1$ and $X^2$ are the same or different and are H or Br, treating the vinyl compound with a metal halide which is cupric bromide, cuprous bromide or ferric bromide, and a base which is DBU or DBN, to form a bromooxazole of the structure

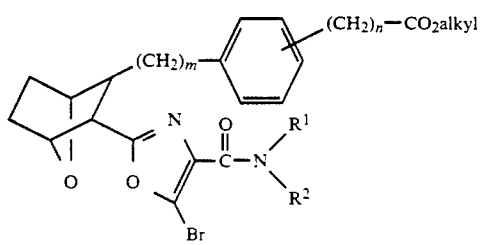

wherein m, n, $R^1$ and $R^2$ are as defined above recovering the bromooxazole, subjecting the bromooxazole to hydrogenolysis by treating the bromooxazole with hydrogen in the presence of a hydrogenolysis catalyst to form the oxazole ester of the structure

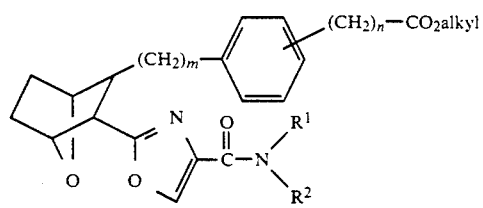

and hydrolyzing the oxazole ester to the acid of the structure

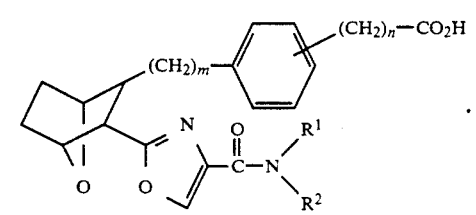

14. The method as defined in claim 13 wherein $R^1$ is hydrogen, $R^2$ is pentyl, m is 1 and n is 2.

15. The method as defined in claim 13 wherein the vinyl compound has the structure

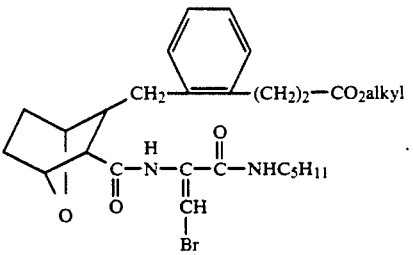

16. The method as defined in claim 13 wherein the vinyl compound has the structure

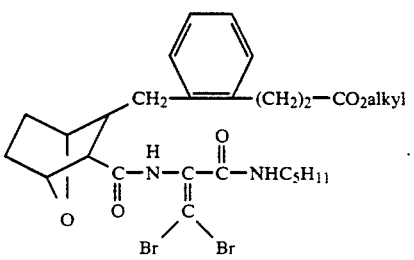

17. The method as defined in claim 13 wherein the metal halide is cupric bromide and the base is DBU.

18. A method for preparing an oxazole acid of the structure

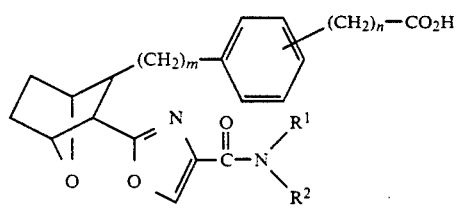

wherein
m is 1, 2 or 3;
n is 0, 1, 2, 3 or 4;
$R^1$ is hydrogen, lower alkyl, aryl, aralkyl, cycloalkyl, cycloalkylalkyl, or an amide of the structure

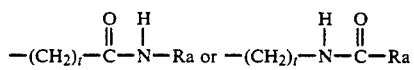

wherein t is 1 to 12 to Ra is lower alkyl, aryl, cycloalkyl or cycloalkylalkyl;
$R^2$ is hydrogen, lower alkyl, aryl, or aralkyl; or
$R^1$ and $R^2$ together with the N to which they are linked form a 5- to 8-membered ring which has only the single N heteroatom, wherein the term "aryl" by itself or as part of another group is phenyl or naphthyl, or phenyl or naphthyl optionally substituted with 1 or 2 substituents which are lower alkyl, trifluoromethyl, halogen, alkylsulfonyl and/or arylsulfonyl; which comprises providing a vinyl compound of the structure

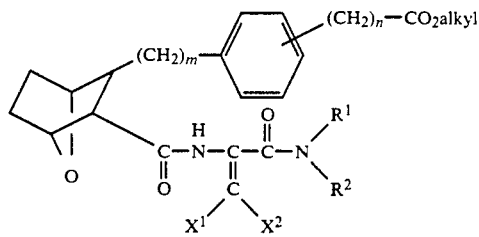

wherein $X^1$ and $X^2$ are the same or different and are H or Br, treating the vinyl compound with a metal halide which is cupric bromide, cuprous bromide or ferric bromide, and a base which is DBU or DBN, to form a bromooxazole of the structure

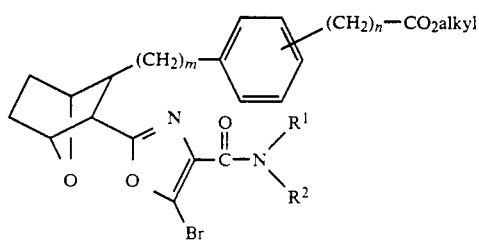

wherein m, n, $R^1$ and $R^2$ are as defined above recovering the bromooxazole, hydrolyzing the bromooxazole to form the corresponding bromooxazole acid of the structure

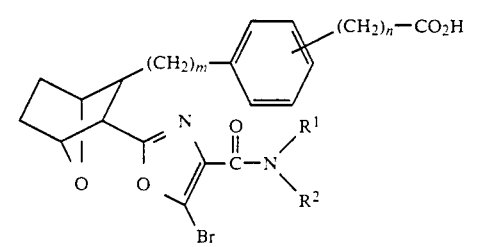

and subjecting the bromooxazole acid to hydrogenolysis by treating the bromooxazole acid with hydrogen in the presence of a reduction catalyst, to form the oxazole of the structure

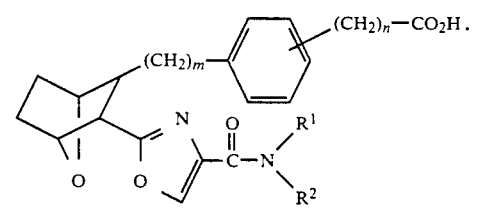

19. The method as defined in claim 18 wherein the hydrogenolysis of the bromooxazole acid is carried out by treating the bromooxazole acid is carried out by treating the bromooxazole acid with weak aqueous base and with hydrogen in the presence of a reduction catalyst to form the corresponding salt, and treating the salt with strong acid to form the oxazole acid.

20. The method as defined in claim 18 wherein $R^1$ is hydrogen, $R^2$ is pentyl, m is 1 and n is 2.

21. The method as defined in claim 18 wherein the vinyl compound has the structure

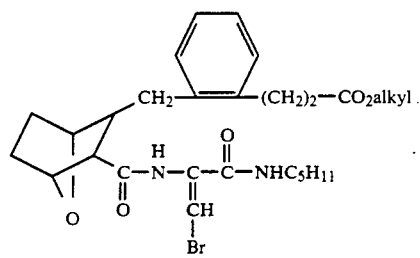

22. The method as defined in claim 18 wherein the vinyl compound has the structure

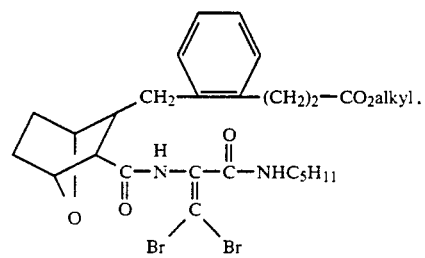

23. The method as defined in claim 18 wherein the metal halide is cupric bromide and the base is DBU.

24. A compound of the structure

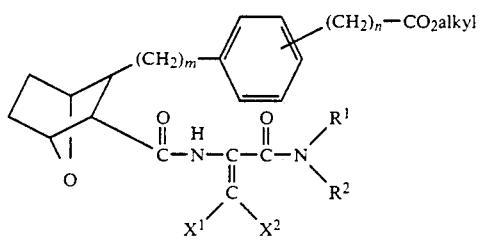

wherein
m is 1, 2 or 3;
n is 0, 1, 2, 3 or 4;
$X^1$ and $X^2$ are each Br;
$R^1$ is hydrogen, lower alkyl, aryl, aralkyl, cycloalkyl, cycloalkylalkyl, or an amide of the structure

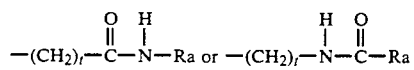

wherein t is 1 to 12 and Ra is lower alkyl, aryl, cycloalkyl or cycloalkylalkyl;
$R^2$ is hydrogen, lower alkyl, aryl, or aralkyl; or
$R^1$ and $R^2$ together with the N to which they are linked form a 5- to 8-membered ring which has only the single N heteroatom, wherein the term "aryl" by itself or as part of another group is phenyl or naphthyl, or phenyl or naphthyl optionally substituted with 1 to 2 substituents which are lower alkyl, trifluoromethyl, halogen, alkylsulfonyl and/or arylsulfonyl.

25. The compound as defined in claim 24 having the structure

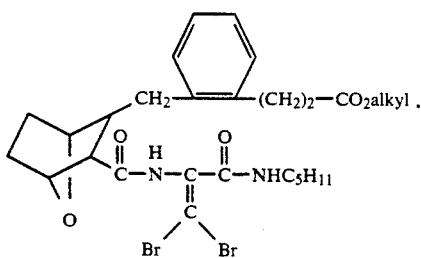

26. A method for preparing a vinyl dibromide as defined in claim 24, which comprises treating a vinyl bromide compound of the structure

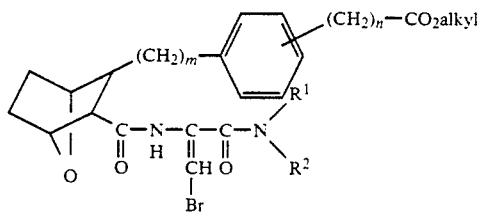

wherein m, n, $R^1$ and $R^2$ are as defined in claim 24, with bromine in the presence of an organic base which is tributylamine triethylamine, or diisopropylethylamine.

27. The method as defined in claim 26 wherein the bromine is employed in a molar ratio to the vinyl bromide within the range of from about 1:1 to about 1.1:1.

28. The method as defined in claim 26 where in the vinyl bromide starting material and vinyl dibromide product, m is 1, n is 2, $R^1$ is H, $R^2$ is $C_5H_{11}$ and the $(CH_2)_2\text{-}CO_2alkyl$ group is linked at the ortho position of the phenyl ring.

29. A method for preparing a bromooxazole of the structure

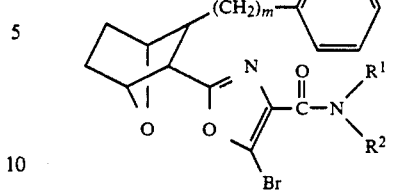

wherein
m is 1, 2 or 3;
n is 0, 1, 2, 3 or 4;
$R^1$ is hydrogen, lower alkyl, aryl, aralkyl, cycloalkyl, cycloalkylalkyl, or an amide of the structure

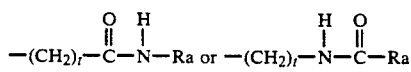

wherein t is 1 to 12 and Ra is lower alkyl, aryl, cycloalkyl or cycloalkylalkyl;
$R^2$ is hydrogen, lower alkyl, aryl, or aralkyl; or
$R^1$ and $R^2$ together with the N to which they are linked form a 5- to 8-membered ring which has only the single N heteroatom, wherein the term "aryl" by itself or as part of another group is phenyl or naphthyl, or phenyl or naphthyl optionally substituted with 1 or 2 substituents which are lower alkyl, trifluoromethyl, halogen, alkylsulfonyl and/or arylsulfonyl, which comprises providing a vinyl compound of the structure

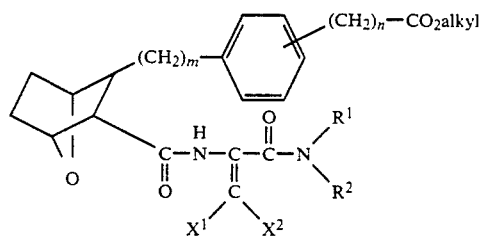

wherein $X^1$ and $X^2$ are each H, treating the above vinyl compound with a bromine source which is $Br_2$ or N-bromosuccinamide, at a reduced temperature of within the range of from about $-80°$ C. to about $-40°$ C., and then with an organic base at a reduced temperature of within the range of from about $-78°$ C. to about $0°$ C., to form the above vinyl compound wherein one of $X^1$ and $X^2$ is Br, treating the so-formed vinyl bromide compound with a metal halide wherein the metal is ferric, cupric or cuprous, and a base which is 1,8-diazabicyclo[5.4.0]-undec-7-ene (DBU) or 1,5-diazabicyclo[4.3.0]non-5-ene (DBN), to convert said vinyl compound to the bromooxazole.

* * * * *

UNITED STATES PATENT AND TRADEMARK OFFICE
CERTIFICATE OF CORRECTION

PATENT NO. : 5,260,449
DATED : November 9, 1993
INVENTOR(S) : J. Singh et al.

It is certified that error appears in the above-identified patent and that said Letters Patent is hereby corrected as shown below:

In Claim 19, Column 23, Lines 62 and 63, delete "is carried out by treating the bromooxazole acid".

Signed and Sealed this

Twenty-sixth Day of July, 1994

Attest:

BRUCE LEHMAN

Attesting Officer    Commissioner of Patents and Trademarks